United States Patent [19]

Guillaume et al.

[11] 4,332,808

[45] Jun. 1, 1982

[54] DOPAMINERGICALLY STIMULATING 4-SUBSTITUTED INDOLES

[75] Inventors: Jacques Guillaume, Sevran; Lucien Nedelec, LeRaincy; Claude Dumont, Nogent-sur-Marne; Robert Fournex, Paris, all of France

[73] Assignee: Roussel Uclaf, Paris, France

[21] Appl. No.: 221,927

[22] Filed: Dec. 31, 1980

Related U.S. Application Data

[63] Continuation-in-part of Ser. No. 154,507, May 29, 1980, abandoned.

[30] Foreign Application Priority Data

Jun. 12, 1979 [FR] France ............................. 79 14976
Oct. 24, 1980 [FR] France ............................. 80 22819

[51] Int. Cl.³ .................. A61K 31/44; A61K 31/445; C07D 401/02
[52] U.S. Cl. .................................. 424/263; 424/267; 546/201; 546/273; 548/469
[58] Field of Search ............... 546/201, 273; 424/267, 424/263

[56] References Cited

U.S. PATENT DOCUMENTS 3,510,491  5/1970  Bell ................................. 546/201 X

OTHER PUBLICATIONS

Chemical Abstracts, 61:16036g (1964) [Bull. Soc. Chim. France 1964(8), 1939–1945, Marc, J., et al.].
Chemical Abstracts, 68:49392x (1968) [C. R. Acad. Sci., Paris, Ser. C 265(2), 110–112 (1967), Marc, J., et al.].

Primary Examiner—Richard A. Schwartz
Attorney, Agent, or Firm—Hammond & Littel, Weissenberger and Muserlian

[57] ABSTRACT

Novel indoles of the formula

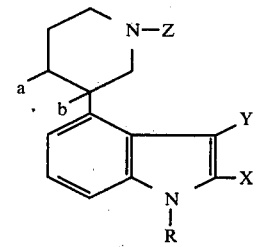

wherein R is selected from the group consisting of hydrogen, alkyl of 1 to 8 carbon atoms and aralkyl of 7 to 12 carbon atoms, X is selected from the group consisting of hydrogen and alkyl of 1 to 18 carbon atoms, Y is selected from the group consisting of hydrogen and halogen, Z is selected from the group consisting of hydrogen, alkyl of 1 to 8 carbon atoms, hydroxy alkyl of 1 to 8 carbon atoms, aryloxyalkyl of 7 to 12 carbon atoms, arylalkyl of 7 to 12 carbon atoms optionally substituted with at least one member of the group consisting of halogen, alkoxy of 1 to 4 carbon atoms, alkyl of 1 to 4 carbon atoms, —OH, —CF₃, —OCF₃, —NO₂ and NH₂, cycloalkylalkyl of 4 to 12 carbon atoms, alkenyl of 3 to 8 carbon atoms and alkynyl of 3 to 8 carbon atoms, and a and b may each be hydrogen or form a double bond or a is hydrogen and b is selected from the group consisting of —OH and alkoxy of 1 to 8 carbon atoms and their non-toxic, pharmaceutically acceptable acid addition salts having dopaminergic stimulating properties optionally accompanied with adrenergic and serotoninergic activity and their preparation and novel intermediates.

16 Claims, No Drawings

DOPAMINERGICALLY STIMULATING 4-SUBSTITUTED INDOLES

PRIOR APPLICATION

This application is a continuation-in-part application of our copending, commonly assigned U.S. patent application Ser. No. 154,507 filed May 29, 1980, now abandoned.

OBJECTS OF THE INVENTION

It is an object of the invention to provide the novel indoles of formula I and their non-toxic, pharmaceutically acceptable acid addition salts and a process and intermediates for their preparation.

It is another object of the invention to provide novel dopaminergic stimulating compositions and to a novel method of inducing dopaminergic stimulating activity in warm-blooded animals.

These and other objects and advantages of the invention will become obvious from the following detailed description.

THE INVENTION

The novel indoles of the invention are selected from the group consisting of compounds of the formula

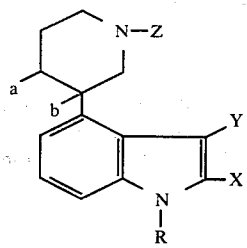

I wherein R is selected from the group consisting of hydrogen, alkyl of 1 to 8 carbon atoms and aralkyl of 7 to 12 carbon atoms, X is selected from the group consisting of hydrogen and alkyl of 1 to 8 carbon atoms, Y is selected from the group consisting of hydrogen and halogen, Z is selected from the group consisting of hydrogen, alkyl of 1 to 8 carbon atoms, hydroxyalkyl of 1 to 8 carbon atoms, aryloxyalkyl of 7 to 12 carbon atoms, arylalkyl of 7 to 12 carbon atoms optionally substituted with at least one member of the group consisting of halogen, alkoxy of 1 to 4 carbon atoms, alkyl of 1 to 4 carbon atoms, —OH, —CF$_3$, —OCF$_3$, NO$_2$ and NH$_2$, cycloalkylalkyl of 4 to 12 carbon atoms, alkenyl of 3 to 8 carbon atoms and alkynyl of 3 to 8 carbon atoms, a and b may each be hydrogen or form a double bond or a is hydrogen and b is selected from the group consisting of —OH and alkoxy of 1 to 8 carbon atoms and their non-toxic, pharmaceutically acceptable acid addition salts.

Examples of suitable acids to form the acid addition salts are mineral acids such as hydrochloric acid, hydrobromic acids, nitric acid, sulfuric acid and phosphoric acid and organic acids such as acetic acid, propionic acid, formic acid benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acid such as benzene sulfonic acid.

Examples of R are hydrogen, alkyl of 1 to 8 carbon atoms such as methyl, ethyl, propyl, isopropyl, butyl, isobutyl, and n-pentyl and aralkyl such as benzyl and phenethyl. X is preferably hydrogen or alkyl of 1 to 4 carbon atoms such as methyl, ethyl, n-propyl and n-butyl. Y is preferably hydrogen or chlorine or bromine.

Examples of Z are alkyl and hydroxy alkyl where the alkyl is methyl, ethyl, n-propyl, isopropyl, n-butyl, isobutyl, n-pentyl and n-hexyl, aryloxyalkyl such as phenoxyethyl or phenoxypropyl, aralkyl such as benzyl, phenethyl or phenylpropyl, optionally substituted with at least one halogen such as bromine or chlorine or alkyl or alkoxy such as methyl, ethyl, methoxy or ethoxy, cycloalkylalkyl such as cyclopropylmethyl, cyclopropylethyl or cyclopropylpropyl, alkenyl such as propenyl and alkynyl such as propargyl. b is preferably alkoxy such as methoxy or ethoxy.

Examples of preferred compounds of formula I are those wherein Y is hydrogen, those wherein X is hydrogen, those wherein Z is hydrogen, those wherein Z is alkyl of 1 to 4 carbon atoms or aralkyl of 7 to 12 carbon atoms and their non-toxic, pharmaceutically acceptable acid addition salts. Also preferred are those compounds of formula I wherein a and b form a double bond, those wherein a and b are hydrogen and those wherein a is hydrogen and b is —OH or CH$_3$O— and their non-toxic, pharmaceutically acceptable acid addition salts.

Specific preferred compounds of formula I are 4-(1-propyl-1,2,5,6-tetrahydropyridin-3-yl)-1H-indole, 4-(1-methyl-1,2,5,6-tetrahydropyridin-3-yl)-1H-indole, 4-(1-methyl-piperidin-3-yl)-1H-indole, 4-(piperidin-3-yl)-1H-indole, 4-(1,2,5,6-tetrahydropyridin-3-yl)-1H-indole, 4-(1-propyl-piperidin-3-yl)-1H-indole, 1-methyl-4-(3-piperidyl)-1H-indole, 1-methyl-4-(1-propyl-3-piperidyl)-1H-indole, 4-(1-ethyl-3-piperidyl)-1H-indole and 4-(1-ethyl-1,2,5,6-tetrahydro-3-pyridyl)-1H-indole and their non-toxic, pharmaceutically acceptable acid addition salts.

The novel process of the invention for the preparation of indoles of formula I comprises reacting a compound of the formula

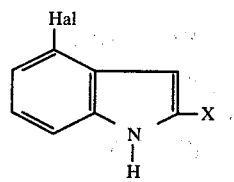

II wherein X is selected from the group consisting of hydrogen and alkyl of 1 to 8 carbon atoms and Hal is a halogen with an alkylation or aralkylation agent to obtain a compound of the formula

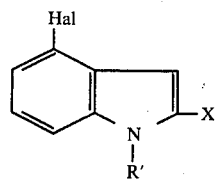

III wherein R' is selected from the group consisting of alkyl of 1 to 8 carbon atoms and aralkyl of 7 to 12 carbon atoms, reacting the latter to form the organo magnesium compound of the formula

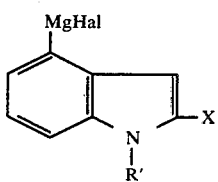

IV condensing the latter with N-benzyl-3-piperidone to obtain a compound of the formula

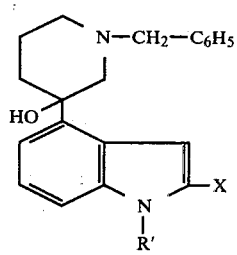

$I_A$ and optionally reacting the latter with a deshydration agent to obtain a compound of the formula

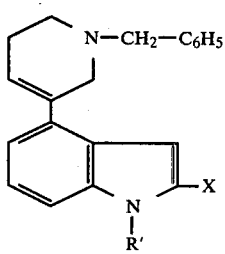

$I_B$ which when R' is benzyl may be reacted with a selective cleavage agent for benzyl on the indole ring to obtain a compound of the formula

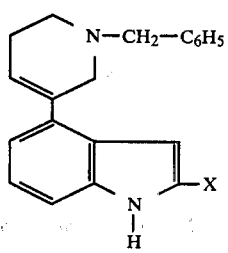

$I_C$ which may be subjected to cleavage with an agent for the benzyl on the tetrahydropyridinyl ring to obtain a compound of the formula

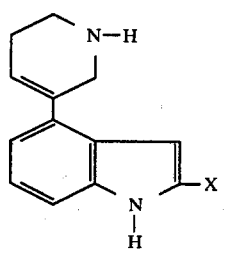

$I_D$ or the compound of formula $I_A$ may be reacted with an agent to cleave the benzyl on the nitrogen atom of tetrahydropyridinyl to obtain a compound of the formula

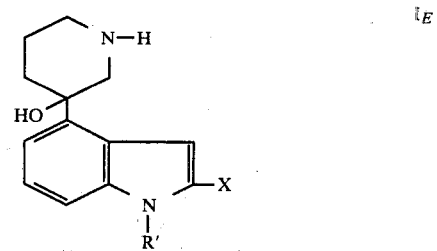

$I_E$ which may be reacted with a deshydration agent to obtain a compound of the formula

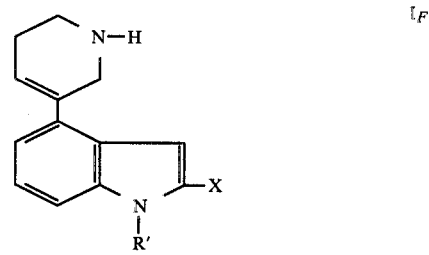

$I_F$ or when R' is benzyl, the compound of formula $I_A$ may be reacted with a selective cleavage agent for the benzyl on the indole ring to obtain a compound of the formula

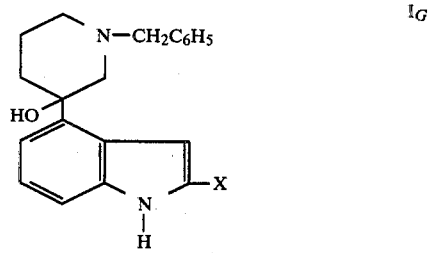

$I_G$ which may be subjected to a cleavage agent for the benzyl on piperidinyl ring to obtain a compound of the formula

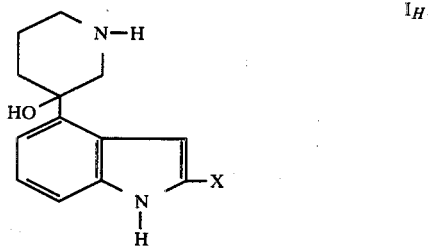

$I_H$ and if desired, reacting each of the compounds of formula I wherein Z is hydrogen with an agent capable of introducing Z' wherein Z' is the same as Z except hydrogen and optionally when b of formula I is —OH, the compound may be etherified to obtain the corresponding compound of formula I where b is alkoxy of 1 to 8 carbon atoms or with a deshydration agent to form the corresponding compound of formula I wherein a and b form a double bond or with an agent to cleave the hydroxy group to obtain the compound of formula I wherein a and b are hydrogen and if desired, each of the compounds of formula I may be reacted with a halogenation agent capable of introduction a 3-halogen on the indole. The acid addition salts of the compounds of formula I may be prepared by treating the compound of formula I with the acid.

It is obvious to one skilled in the art that a certain number of steps of the process may be effected in a different order. The process is naturally not to be limited to the number of steps or a determined order of the steps.

In a preferred mode of the process of the invention, the halogen of the compound of formula II is chlorine or bromine and the alkylation or aralkylation agent is preferably an alkyl or aralkyl halide where the halide is the chloride, bromide or iodide. The formation of the organo-magnesium derivative of formula IV is formed by reaction of compound of formula III with magnesium in an appropriate solvent, especially tetrahydrofuran, in the presence of a small amount of dibromoethane or by an exchange reaction with an organo metallic derivative such as butyllithium. The deshydration agent is a strong acid such as hydrochloric acid, oxalic acid or phosphoric acid anhydride and the agent to cleave the benzyl from the indole ring is sodium in ammonia at low temperatures. If a and b do not represent a double bond, the benzyl group may be cleaved from the piperidinyl ring with hydrogen in the presence of a catalyst such as palladium. To cleave the benzyl group of the compound of formula $I_C$, it is preferable to use ethyl chloroformate to form the corresponding ethyl carbamate which is hydrolyzed in an alkaline medium to form the compound of formula $I_D$. The introduction of Z' is preferably effected with a Z'-Hal wherein Hal is chlorine, bromine or iodine. The preferred etherification group of OH group is an alcohol in an anhydrous acid medium and the cleavage of the hydroxy group is preferably effected with lithium in liquid ammonia at low temperatures such as $-35°$ to $-60°$ C. The halogenation of the 3-position of the indole is preferably effected with a N-halosuccinimide such as N-chloro or N-bromo-succinimide in an appropriate solvent such as dioxane.

The starting compounds of formula II are generally known products which may be prepared, for example, by the process described in Gazz. Chim. Ital., Vol. 88 (1958), p. 1147. N-benzyl-3-piperidinone is a known, commercially available compound.

The novel intermediates of the invention are compounds of the formula

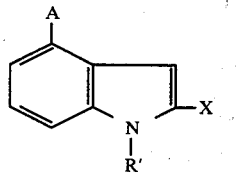

wherein A is selected from the group consisting of -Hal and -MgHal, Hal is halogen, X is selected from the group consisting of hydrogen and alkyl of 1 to 8 carbon atoms and R' is selected from the group consisting of alkyl of 1 to 8 carbon atoms and aralkyl of 7 to 12 carbon atoms. Particularly preferred are 4-chloro-1-benzyl-1H-indole and its magnesium derivative.

The novel dopaminergic stimulating compositions of the invention are comprised of a dopaminergically stimulating amount of at least one compound of formula I and its non-toxic, pharmaceutically acceptable acid addition salts and an inert pharmaceutical carrier or excipient. The compositions may be in the form of tablets, dragees, gelules, capsules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives. The compositions may also possess adrenergic and serotoninergic activity.

The compositions are useful for the treatment of numerous maladies or diverse pathological disorders. They are useful for the treatment of neurological syndromes of extra pyramidal origin such as for the treatment of Parkinson's disease and the treatment of post-encephalitic parkinson syndromes, for the treatment of prolactin hypersecretion antehypophysis such as in the treatment of hypogonadism in the male or female. The compositions are also useful for the treatment of cerebral senescence, vertebrobasilany insufficiency, arterial hypertension, peripherial circulatory troubles and in the treatment of arteriopathy of lower limbs and of trophic complications.

The novel method of inducing dopaminergic stimulating activity in warm-blooded animals, including humans, comprises administering to warm-blooded animals a dopaminergically stimulating effective amount of at least one compound of formula I and its non-toxic, pharmaceutically acceptable acid addition salts. The compounds may be administered orally, rectally or parenterally. The effective daily dose is dependent on the conditions treated and the specific compound. For the treatment of Parkinson disease or cerebral senescence, the usual daily dose is 0.1 to 20 mg/kg by oral route in the man.

In the following examples there are described several preferred embodiments to illustrate the invention. However, it should be understood that the invention is not intended to be limited to the specific embodiments.

EXAMPLE 1

1-benzyl-3-[1-benzyl-1H-indole-4-yl]-3-piperidinol hydrochloride

STEP A: 4-chloro-1-benzyl-1H-indole

A mixture of 16.9 g of 4-chloro-1H-indole, 170 ml of benzene, 85 ml of aqueous 50% sodium hydroxide solution, 1.89 g of n-tetrabutyl ammonium hydrogen sulfate and 16.6 ml of benzyl chloride was heated at 60° C. with strong stirring for 4 hours and was then cooled to room temperature. The decanted organic phase was washed with water, dried and evaporated to dryness. The 30.2 g of residue were chromatographed over silica gel and were eluted with cyclohexane to obtain 22.8 g of 4-chloro-1-benzyl-1H-indole melting at 58°–60° C.

STEP B: 1-benzyl-3-[1-benzyl-1H-indole-4-yl]-3-piperidinol hydrochloride

A mixture of 113 g of magnesium in 200 ml of tetrahydrofuran was refluxed while a solution of 184 g of the product of Step A in 20 ml of 1,2-dibromoethane and 300 ml of tetrahydrofuran were added slowly thereto and the mixture was then refluxed for 3 hours and cooled to 30° C. to obtain a magnesium solution to which a solution of 128 g of N-benzyl-3-piperidone in 250 ml of tetrahydrofuran was added while keeping the temperature below 35° C. The mixture was refluxed for 2 hours and then was cooled to 20° C. Then one liter of an aqueous saturated ammonium chloride solution was slowly added thereto and 2 liters of ethyl acetate were added thereto. The mixture was filtered and the decanted ethyl acetate phase was washed with water, dried and evaporated to dryness. The 330 g of residue were chromatographed over silica gel and were eluted with a 9-1 cyclohexane-triethylamine mixture to obtain 218.4 g of product which was dissolved in ethyl acetate. The solution was extracted with 1 N hydrochloric acid and the aqueous phase was made alkaline by addition of ammonium hydroxide. The mixture was extracted with ethyl acetate and the organic phase was dried. 100 ml of ethyl acetate saturated with gaseous hydrogen chloride were added to the organic phase and the mixture was filtered. The recovered product was washed with ethyl acetate, with ether and dried to obtain 194 g of 1-benzyl-3-[1-benzyl-1H-indole-4-yl]-3-piperidinol hydrochloride melting at 185° C. Crystallization from ethyl acetate containing 10% methanol yielded the pure product melting at 190° C. The free base was obtained by treating the hydrochloride salt with sodium hydroxide, extracting the aqueous phase with ethyl acetate and evaporating the organic phase to dryness.

EXAMPLE 2

1-benzyl-3-(1H-indol-4-yl)-3-piperidinol hydrochloride 500 ml of ammonia and then 1.5 g of sodium were progressively added at −40° C. to a solution of 14.8 g of 1-benzyl-3-[1-benzyl-1H-indol-4-yl]-3-piperidinol in 250 ml of tetrahydrofuran and after the addition was complete, ammonium chloride was added to the mixture until the faint blue coloration disappeared. The residue was taken up in water and the aqueous phase was extracted with ethyl acetate. The organic phase was washed with water, dried and evaporated to dryness to obtain 12 g of 1-benzyl-3-(1H-indol-4-yl)-3-piperidinol.

The said 12 g were dissolved in ethyl acetate and ethyl acetate saturated with gaseous hydrogen chloride was added thereto. The mixture was filtered and the recovered product was washed with ethyl acetate and was dried to obtain 12.7 g of 1-benzyl-3-(1H-indol-4-yl)-3-piperidinol hydrochloride melting at 228°–230° C.

EXAMPLE 3

4-[1-benzyl-1,2,5,6-tetrahydropyridin-3-yl]-1H-indole oxalate

A mixture of 8 g of the product of Example 2 in 200 ml of 1 N hydrochloric acid was heated to reflux and was then cooled to 20°–25° C. and was poured into a mixture of ice and water. Concentrated ammonium hydroxide was added to the mixture which was then extracted with ethyl acetate. The organic phase was dried and evaporated to dryness to obtain 6.35 g of residue. The residue was chromatographed over silica gel and was eluted with a 9-1 cyclohexane-triethylamine mixture to obtain 4 g of 4-[1-benzyl-1,2,5,6-tetrahydropyridin-3-yl]-1H-indole.

3.6 g of said product were dissolved in 200 ml of isopropanol and 1.5 g of oxalic acid dihydrate were added thereto. The mixture was refluxed while adding methanol thereto and the methanol was distilled under reduced pressure. The mixture was cooled to 0° C. and was vacuum filtered and the recovered product was dried to obtain 4.2 g of 4-[1-benzyl-1,2,5,6-tetrahydropyridyn-3-yl]-1H-indole oxalate melting at 202° C.

EXAMPLE 4

3-(1H-indol-4-yl)-3-piperidinol hydrochloride

A mixture of 12.7 g of 1-benzyl-3-(1H-indol-4-yl)-piperidinol hydrochloride in 500 ml of methanol containing 3.6 g of palladized carbon was hydrogenated at 60° C. and the mixture was then filtered. The filtrate was evaporated to dryness to obtain 9 g of 3-(1H-indol-4-yl)-3-piperidinol hydrochloride. The free base was obtaining by dissolving the product in aqueous sodium hydroxide, extraction with ethyl acetate and evaporation of the organic phase to dryness.

EXAMPLE 5

1-methyl-3-(1H-indol-4-yl)-3-piperidinol neutral oxalate 5.8 g of a solution of 40% aqueous formal were added at 0° to −5° C. to a mixture of 13.3 g of 3-(1H-indol-4-yl)-3-piperidinol in 120 ml of methanol and after stirring the mixture for 15 minutes, 4.9 g of 95% sodium borohydride were added thereto. Water was added to the mixture which was then extracted with chloroform containing 20% of methanol. The organic phase was washed with water, dried over magnesium sulfate and filtered. The filtrate was evaporated to dryness and the 11.8 g of residue were crystallized from benzene to obtain 9 g of 1-methyl-3-(1H-indol-4-yl)-3-piperidinol melting 145° C.

4.5 g of the said product were dissolved in 500 ml of hot isopropanol and 1.2 g of oxalic acid dihydrate were added thereto. 200 ml of methanol were added to the mixture which was refluxed. The methanol was evaporated and the mixture was iced and vacuum filtered. The recovered product was dried to obtain 4.95 g of 1-methyl-3-(1H-indol-4-yl)-3-piperidinol neutral oxalate melting at 250° C.

EXAMPLE 6

4-(1-methyl-1,2,5-6-tetrahydropyridin-3-yl)-1H-indole neutral oxalate

A solution of 4.8 g of 1-methyl-3-(1H-indole-4-yl)-piperidinol in 150 ml of 1 N hydrochloric acid was refluxed for 5 hours and was then cooled and diluted with water. Concentrated ammonium hydroxide was added to the mixture which was then extracted with chloroform containing 10% methanol. The organic phase was dried and evaporated to dryness to obtain 4.4 g of residue. The latter was chromatographed over silica gel and was eluted with a 6-3-1cyclohexane-chloroform-triethylamine mixture to obtain 2.8 g of 4-(1-methyl-1,2,5,6-tetrahydropyridin-3-yl)-1H-indole melting at 175° C.

2.4 g of the said product were dissolved in 200 ml of refluxing isopropanol and 630 mg of oxalic acid dihydrate were added to the solution. The precipitate was dissolved in methanol and the solution was concentrated to 100 ml. The mixture was iced and filtered to obtain 2.6 g of 4-(1-methyl-1,2,5,6-tetrahydropyridin-3-yl)-1H-indole neutral oxalate melting at 232° C.

EXAMPLE 7

4-(1-propyl-1,2,5,6-tetrahydropyridin-3-yl)-1H-indole acid fumarate

A suspension of 6 g of 3-(1H-indol-3-yl)-piperidinol hydrochloride, 120 ml of dimethylformamide, 7.5 g of sodium carbonate and 2.8 g of propyl iodide was stirred for 4 hours at room temperature and was then diluted with water. The mixture was extracted with ethyl acetate and the organic phase was dried and evaporated to dryness. The 5.5 g of residue were chromatographed over silica gel and eluted with a 6-3-1 cyclohexane-chloroform-triethylamine mixture to obtain 4.85 g of 1-propyl-3-(1H-indole-4-yl)-3-piperidinol.

4.8 g of the said product were dissolved in 150 ml of 1 N hydrochloric acid and the mixture was refluxed for 2 hours and cooled to room temperature. The mixture was made alkaline and was extracted with ethyl acetate. The organic phase was dried over magnesium sulfate, filtered and the filtrate was evaporated to dryness to obtain 4.3 g of residue. The latter was chromatographed over silica gel and was eluted with a 6-3-1 cyclohexane-chloroform-triethylamine mixture to obtain 2.9 g of 4-(1-propyl-1,2,5,6-tetrahydropyridin-3-yl)-1H-indole.

2.7 g of the said product were dissolved in 200 ml of ethanol and 1.3 g of fumaric acid was added thereto. The acid dissolved and a crystallization started. The mixture was vacuum filtered and the product was crystallized from ethanol to obtain 2.8 g of 4-(1-propyl-1,2,5,6-tetrahydropyridin-3-yl)-1H-indole acid fumarate melting at 168° C.

EXAMPLE 8

1-phenethyl-3-(1H-indol-4-yl)-3-piperidinol

A suspension of 6 g of 3-(1H-indol-3-yl)-3-piperidinol hydrochloride, 120 ml of dimethylformamide, 7.5 g of sodium carbonate and 3.9 ml of β-phenethyl bromide was heated at 50° C. for 3 hours and was then poured into water. The mixture was extracted with ethyl acetate and the organic phase was dried over magnesium sulfate and filtered and the filtrate was evaporated to dryness. The 8.9 g of residue were chromatographed over silica gel and eluted with 6-3-1-cyclohexane-chloroform-triethylamine mixture to obtain 6.9 g of 1-phenethyl-3-(1H-indol-4-yl)-3-piperidinol.

EXAMPLE 9

4-[1-phenethyl-1,2,5,6-tetrahydropyridin-3-yl]-1H-indole acid fumarate

A solution of 6.3 g of the product of Example 8 in 150 ml of 1 N hydrochloric acid was refluxed for 2½ hours and was cooled to 20°-25° C. and diluted with water. The solution was made alkaline by addition of sodium hydroxide solution and was extracted with ethyl acetate. The organic phase was dried and evaporated to dryness to obtain 6.2 g of residue. The latter was chromatographed over silica gel and was eluted with a 6-3-1 cyclohexane-chloroform-triethylamine mixture to obtain 4.7 g of 4-[1-phenethyl-1,2,5,6-tetrahydropyridin-3yl]-1H-indole.

The said product was dissolved in 100 ml of hot isopropanol and 1.8 g of fumaric acid were added thereto during which crystallized occured. The crystals were redissolved at reflux while adding 200 ml of isopropanol and the mixture was concentrated to 200 ml. The mixture was iced and vacuum filtered to obtain 5.4 g of product which was crystallized from ethyl acetate containing 60% methanol to obtain 3.9 g of 4-[1-phenethyl-1,2,5,6-tetrahydropyridin-3-yl]-1H-indole acid fumarate melting at 205° C.

EXAMPLE 10

4-(1-methyl-piperidin-3-yl)-1H-indole neutral fumarate 2.6 g of lithium were added in small portions at −40° C. to a stirred mixture of 200 ml of ammonia, 40 ml of tetrahydrofuran, 20 ml of anhydrous ethanol and 5 g of 1-methyl-3-(1H-indol-3-yl)-3-piperidinol and the mixture was stirred at −40° C. for 30 minutes. Ammonium chloride was added to the mixture and the ammonia was evaporated at room temperature. The residue was taken up in 100 ml of water and the aqueous phase was extracted with ethyl acetate. The organic phase was dried and evaporated to obtain 4.65 g of residue. The latter was chromatographed over silica gel and was eluted with a 95-5 chloroform-methanol mixture to obtain 3 g of 4-(1-methyl-piperidin-3-yl)-1H-indole melting at 151° C.

2.7 g of the said product were dissolved in 100 ml of isopropanol and 800 mg of fumaric acid were added thereto. The mixture was refluxed while methanol was added for complete dissolution and the mixture was filtered hot. The methanol was evaporated under reduced pressure at 40° C. and the mixture was iced and filtered. The recovered product was washed with isopropanol and dried to obtain 3 g of 4-(1-methyl-piperidin-3-yl)-1H-indole neutral fumarate melting at 260° C.

EXAMPLE 11

4-(piperidin-3-yl)-1H-indole hydrochloride 700 mg of lithium were added in small fractions over one hour at −40° C. to a mixture of 100 ml of ammonia, 1.2 g of 3-(1H-indol-4-yl)-3-piperidinol hydrochloride, 20 ml of tetrahydrofuran and 10 ml of anhydrous ethanol and the ammonia was evaporated at room temperature. The residue was taken up in 100 ml of water and the aqueous phase was extracted with chloroform containing 10% methanol. The organic phase was washed with water, dried and filtered. The filtrate was evaporated to dryness and the 950 mg of residue was chromatographed over silica gel. Elution with a 7-2-1-chloroform-methanol-triethylamine mixture yielded 665 mg of 4-(piperidin-3-yl)-1H-indole.

2.3 g of the said product were dissolved in 50 ml of ethyl acetate and ethyl acetate saturated with gaseous hydrogen chloride was added thereto. The mixture was filtered and the recovered product was washed with ethyl acetate and dried and crystallized from acetonitrile containing 20% methanol to obtain 2.2 g of 4-(piperidin-3-yl)-1H-indole hydrochloride.

EXAMPLE 12

4-(1,2,5,6-tetrahydropyridin-3-yl)-1H-indole neutral oxalate

A mixture of 7.6 g of 3-(1H-indol-4-yl)-3-piperidinol in 300 ml of 1 N hydrochloric acid was refluxed and was then cooled to 20°-25° C. and ammonium hydroxide was added thereto. The mixture was extracted with chloroform containing 20% methanol and the organic phase was dried and evaporated to dryness to obtain 7 g of residue. The latter was chromatographed over silica gel and was eluted with a 6-3-1 chloroform-acetone-triethylamine mixture to obtain 3.4 g of product which was empasted with acetone and ether. The product was washed with ether and dried to obtain 3 g of 4-(1,2,5,6-tetrahydropyridin-3-yl)-1H-indole melting at 156° C.

The said 3 g of product were dissolved in 30 ml of isopropanol and 1.9 g of oxalic acid dihydrate were added thereto. 3.8 g of product were crystallized from methanol to obtain 3.3 g of 4-(1,2,5,6-tetrahydropyridin-3-yl)-1H-indole neutral oxalate melting at 230° C.

EXAMPLE 13

4-(3-methoxy-piperidin-3-yl)-1H-indole oxalate 1.5 g of 3-(1H-indol-4-yl)-3-piperidinol hydrochloride were dissolved in 20 ml of methanol and 10 ml of methanol saturated with hydrogen chloride and the solution was held at 20°-25° C. for 7 hours and was then poured into water. The aqueous phase was made alkaline by addition of sodium carbonate and the mixture was filtered. The recovered product was washed with water and dried to obtain 900 mg of product. Crystallization from ethyl acetate yielded 4-(3-methoxy-piperidin-3-yl)-1H-indole melting at 212° C.

2.55 g of the said product were dissolved in 200 ml of isopropanol at 40°-50° C. and 1.4 g of oxalic acid dihydrate were added thereto. The precipitate was redissolved by addition of methanol and the solution was concentrated to 100 ml, iced and filtered. The recovered product was dried to obtain 2.7 g of 4-(3-methoxy-piperidin-3-yl)-1H-indole oxalate melting at 218° C.

EXAMPLE 14

1-benzyl-4-(1,2,5,6-tetrahydropyridin-3-yl)-1H-indole hydrochloride

STEP A: 3-[1-benzyl-1H-indol-4-yl]-3-piperidinol hydrochloride

A mixture of 14.4 g of 1-benzyl-3-[1-benzyl-1H-indol-4-yl]-piperidinol hydrochloride in 600 ml of methanol containing 4.3 g of 10% palladized carbon was hydrogenated at 40° C. and the mixture was cooled to room temperature and filtered. The filter was rinsed with methanol and the filtrate was evaporated to dryness at 40° C. under reduced pressure to obtain 10.65 g of 3-[1-benzyl-1H-indol-4-yl]-3-piperidinol hydrochloride with an Rf=0.35 (7-2-1 chloroform-methanol-triethylamine elutant-silica gel).

STEP B: 1-benzyl-4-(1,2,5,6-tetrahydropyridin-3-yl)-1H-indole hydrochloride

A mixture of 10.4 g of the product of Step A in 500 ml of 1 N hydrochloric acid was refluxed for 2 hours and the mixture was cooled and diluted with water. Sodium hydroxide was added to the mixture which was then extracted with ethyl acetate. The organic phase was dried and evaporated to dryness to obtain 7 g of residue which was chromatographed over silica gel. Elution with a 6-3-1 cyclohexanechloroform-triethylamine yielded 4.7 g of 1-benzyl-4-(1,2,5,6-tetrahydropyridin-3-yl)-1H-indole in the form of a brown oil.

The said oil was dissolved in 200 ml of ethyl acetate and ethyl acetate solution saturated with gaseous hydrogen chloride was added thereto at 0° to 5° C. The mixture was filtered and the product was rinsed with ethyl acetate and dried under reduced pressure at 40° C. to obtain 4.7 g of 1-benzyl-4-(1,2,5,6-tetrahydropyridin-3-yl)-1H-indole hydrochloride melting at 168° C. after crystallization from isopropanol.

EXAMPLE 15

1-benzyl-4-[1-benzyl-1,2,5,6-tetrahydropyridin-4-yl]-1H-indole acid oxalate

A mixture of 53 g of 1-benzyl-4-[1-benzyl-1,2,5,6-tetrahydropyridin-3-yl]-3-piperidinol in 2000 ml of 1 N hydrochloric acid was refluxed for 7 hours and then stood over night at room temperature. The mixture was diluted with water and made alkaline by sodium hydroxide addition. The mixture was extracted with ethyl acetate after salting out with potassium carbonate. The organic phase was washed with water dried over magnesium sulfate and was filtered and the filtrate was evaporated to dryness under reduced pressure. The 55 g of residue were chromatographed over silica gel and eluted with a 9-1 chloroform-acetone mixture to obtain 31 g of purified 1-benzyl-4-[1-benzyl-1,2,5,6-tetrahydropyridin-3-yl]-1H-indole as a brown oil.

3.6 g of the said product were dissolved in 200 ml of ethanol at 40° C. and 1.2 g of oxalic acid dihydrate were added thereto. The hot mixture was filtered and the filtrate was concentrated to about 100 ml and was iced and filtered. The product was washed and dried to obtain 3.8 g of 1-benzyl-4-[1-benzyl-1,2,5,6-tetrahydropyridin-4-yl]-1H-indole acid oxalate melting at 154° C.

EXAMPLE 16

4-[1-benzyl-piperidin-3-yl]-1H-indole neutral succinate

A solution of 33.5 g of 1-benzyl-4-[1-benzyl-1,2,5,6-tetrahydropyridin-3-yl]-1H-indole, 300 ml of tetrahydrofuran and 500 ml of ammonia was stirred at −50° C. for 2 hours and then 8.5 g of sodium were added thereto at −40° C. Ammonium chloride was added thereto and the ammonia was evaporated. The residue was taken up in water and the solution was extracted with ethyl acetate to obtain 26.80 g of residue. The latter was chromatographed over silica gel and eluted with a 6-3-1 cyclohexane-chloroform-triethylamine mixture to obtain 22.3 g of 4-[1-benzyl-piperidin-3-yl]-1H-indole in the form of an oil.

4 g of the said product were dissolved in 300 ml of refluxing isopropanol and 1.6 g of succinic acid were added thereto. The precipitate was redissolved by addition of 200 ml of isopropanol and 200 ml of methanol and the hot solution was filtered and concentrated to 200 ml. The mixture was iced and filtered and the recovered product was washed and dried under reduced pressure to obtain 4 g of 4-[1-benzylpiperidin-3-yl]-1H-indole neutral succinate melting at 210° C.

EXAMPLE 17

4-[1-propyl-piperidin-3-yl]-1H-indole neutral fumarate 3.8 g of sodium carbonate and 2.2 ml of propyl iodide were added to a mixture of 3.5 g of 4-(piperidin-3-yl)-1H-indole in 70 ml of dimethylformamide and the mixture was stirred for 5 hours and diluted with water. The aqueous phase was extracted with ethyl acetate and the organic phase was washed with water, dried over magnesium sulfate and filtered. The filtrate was evaporated to dryness to obtain 4.1 g of residue and the latter was chromatographed over silica gel. Elution with a 6-3-1 cyclohexane-chloroform-triethylamine mixture yielded 3.9 g of 4-(1-propyl-piperidin-3-yl)-1H-indole.

The 3.9 g of product was dissolved in 200 ml of isopropanol and 1 g of fumaric acid was added thereto.

The mixture was refluxed for 10 minutes and was concentrated to about 100 ml. Crystallization was induced by seeding and the mixture was vacuum filtered. The crystals were washed and dried to obtain 3.5 g of 4-[1-propyl-piperidin-3-yl]-1H-indole neutral fumarate melting at 185° C.

EXAMPLE 18

1-benzyl-3-[1-methyl-1H-indol-4-yl]-3-piperidinol hydrochloride

STEP A: 1-methyl-4-chloro-1H-indole

A mixture of 60 g of 4-chloro-1H-indole, 400 ml of benzene, 200 ml of 50% sodium hydroxide solution, 68 g of n-tetrabutylammonium hydrogen sulfate and 68 ml of methyl iodide was stirred at 40° C. for 4 hours and was then cooled. The decanted aqueous phase was extracted with ethyl acetate and the combined organic phases were washed with aqueous sodium chloride, dried over magnesium sulfate and distilled to dryness under reduced pressure. The residue was chromatographed over silica gel and was eluted with an 8-2 cyclohexanebenzene mixture to obtain 63.85 g of 1-methyl-4-chloro-1H-indole.

STEP B: 1-benzyl-3-[1-methyl-1H-indol-4-yl]-3-piperidinol hydrochloride

A mixture of 12 g of magnesium in 155 ml of tetrahydrofuran was refluxed while a solution of 38 g of 1-methyl-4-chloro-1H-indole, 4.5 ml of 1,2-dibromoethane and 115 ml of tetrahydrofuran was slowly added thereto. After the addition of a few drops of methyl iodide, the mixture was refluxed for 6 hours and was then cooled to 45° C. to form a solution to which a solution of 1-benzyl-3-piperidone (prepared from 50 g of 1-benzyl-3-piperidone hydrochloride) in 115 ml of tetrahydrofuran was added dropwise. The mixture was refluxed for 2 hours and then allowed to cool to room temperature. The mixture was stirred for 16 hours and was then cooled in an ice bath while 200 ml of an aqueous saturated ammonium chloride solution was added dropwise thereto. The mixture was filtered and the filter was rinsed with water and ethyl acetate. The decanted aqueous phase was extracted with ethyl acetate and the organic phase was washed with aqueous sodium chloride solution and was evaporated to dryness under reduced pressure. The residue was taken up in ether and the solution was extracted with 1 N hydrochloric acid. The aqueous phase was made alkaline and was extracted with ethyl acetate. The organic phase was evaporated to dryness under reduced pressure and the 73.4 g of residue were chromatographed over silica gel. Elution with a 9-1 cyclohexane-triethylamine mixture yielded a product which was taken up in methylene chloride. The solution was filtered and the filtrate was evaporated to dryness under reduced pressure to obtain 60.5 g of 1-benzyl-3-[1-methyl-1H-indol-4-yl]-3-piperidinol.

The said base was dissolved in 300 ml of ethyl acetate and a solution of hydrogen chloride in ethyl acetate was added to the solution dropwise until the pH was 4. The mixture was iced for 16 hours and was vacuum filtered and the recovered product was washed with ethyl acetate and dried at 50° C. under reduced pressure to obtain 59.6 g of 1-benzyl-3-[1-methyl-1H-indol-4-yl]-3-piperidinol hydrochloride melting at 250° C.

Analysis: $C_{21}H_{25}N_2O$: molecular weight=356.90. Calculated: %C 70.67; %H 7.06; %N 7.85; %Cl 9.93. Found: %C 70.4; %H 6.9; %N 7.9; %Cl 10.1.

EXAMPLE 19

3-[1-methyl-1H-indol-4-yl]-3-piperidinol hydrochloride

A mixture of 50 g of the product of Example 18, 15 g of palladized carbon and 1.5 liters of methanol was hydrogenated at 40° C. and the mixture was then cooled and filtered. The filtrate was evaporated to dryness under reduced pressure to obtain 37 g of 3-[1-methyl-1H-indol-4-yl]-3-piperidinol hydrochloride with an Rf=0.3 (silica gel-Eluant 6-3-1 chloroform-methanol-triethylamine mixture).

EXAMPLE 20

1-methyl-4-(1,2,5,6-tetrahydropyridin-3-yl)-1H-indole neutral oxalate

A solution of 12 g of the product of Example 19 in 360 ml of 1 N hydrochloric acid was refluxed for 4 hours and was cooled in an ice bath while adding sodium hydroxide solution until the pH was alkaline. The mixture was extracted with methylene chloride and the organic phase was washed with aqueous sodium chloride solution, dried over magnesium sulfate and distilled to dryness under reduced pressure. The residue was chromatographed over silica gel and was eluted with a 6-3-1 chloroform-acetone-triethylamine mixture to obtain 6 g of 1-methyl-4-(1,2,5,6-tetrahydropyridin-3-yl)-1H-indole.

6 g of the said product were dissolved in 60 ml of isopropanol and a solution of 1.75 g of oxalic acid in 35 ml of isopropanol was added thereto. The mixture was iced and vacuum filtered and the recovered product was washed with isopropanol and dried under reduced pressure at 50° C. to obtain 5.4 g of 1-methyl-4-(1,2,5,6-tetrahydropyridin-3-yl)-1H-indole neutral oxalate melting at 230° C. after crystallization from methanol.

EXAMPLE 21

1-propyl-3-(1-methyl-1H-indol-4-yl)-3-piperidinol 14.5 g of sodium carbonate and 6 ml of propyl iodide were added to a mixture of 12 g of 3-(1-methyl-1H-indol-4-yl)-3-piperidinol hydrochloride in 240 ml of dimethylformamide and the mixture was stirred for 20 hours and then was diluted with water. The mixture was extracted with ethyl acetate and the organic phase was washed with aqueous sodium chloride solution, dried and evaporated to dryness under reduced pressure. The 11 g of residue were chromtographed over silica gel and eluted with a 9-1 cyclohexane-triethylamine mixture to obtain 8.2 g of 1-propyl-3-(1-methyl-1H-indol-4-yl)-3-piperidinol with an Rf=0.2.

EXAMPLE 22

1-methyl-4-[1-propyl-1,2,5,6-tetrahydropyridin-3yl]-1H-indole acid oxalate

A solution of 8.2 g of 1-propyl-3-(1-methyl-1H-indol-4-yl)-3-piperidinol in 250 ml of 1 N hydrochloric acid was refluxed for 4 hours and while cooling in an ice bath, sodium hydroxide solution was added thereto until the pH was alkaline. The mixture was extracted with methylene chloride and the organic phase was washed with aqueous sodium chloride solution, dried and evaporated to dryness under reduced pressure. The residue was chromatographed over silica gel and was eluted with a 9-1 cyclohexane-triethylamine mixture to obtain 6.2 g of 1-methyl-4-(1-propyl-1,2,5,6-tetrahydropyridin-3-yl)-1H-indole with an Rf=0.2.

6.2 g of the said product were dissolved in 62 ml of isopropanol and a solution of 3 g of oxalic acid in 30 ml of isopropanol was added thereto. The precipitate was redissolved by heating and crystallization was induced. The mixture was iced for 16 hours and was vacuum filtered and the recovered product was washed with isopropanol and dried under reduced pressure to obtain 7.5 g of 1-methyl-4-[1-propyl-1,2,5,6-tetrahydropyridin-3-yl]-1H-indole acid oxalate melting at 163° C. after crystallization from ethanol.

EXAMPLE 23

1-methyl-3-(1-methyl-1H-indol-4-yl)-3-piperidinol

A solution of 16.5 g of 3-(1-methyl-1H-indol-4-yl)-3-piperidinol hydrochloride in 20 volumes of water was iced and made alkaline by addition of sodium hydroxide. The mixture was extracted with ethyl acetate and the organic phase was washed with water, dried over magnesium sulfate and evaporated to dryness under reduced pressure. The residue was dissolved in 150 ml of methanol and 7 ml of a 40% formaldehyde solution were added thereto at 10° C. After 15 minutes, the mixture was cooled to 5° C. and 5 g of sodium borohydride were added thereto in small amounts. The mixture was stirred for one hour and was then diluted with water. The mixture was extracted with methylene chloride and the organic phase was washed with water, dried and evaporated to dryness under reduced pressure to obtain 15 g of residue melting at 80° C. The residue was chromatographed over silica gel and was eluted with a 9-1 cyclohexane-triethylamine mixture to obtain 1-methyl-3-(1-methyl-1H-indol-4-yl)-3-piperidinol melting at 90° C.

EXAMPLE 24

1-methyl-4-(1-methyl-1,2,5,6-tetraydropyridin-3-yl)-1H-indole acid oxalate

A solution of 15 g of 1-methyl-3-(1-methyl-1H-indol-4-yl)-3-piperidinol in 500 ml of 1 N hydrochloric acid was refluxed for 3 hours and was then cooled to room temperature and stirred for 16 hours. The mixture was cooled in an ice bath while adding sodium hydroxide until the mixture was alkaline and the mixture was extracted with ethyl acetate. The organic phase was washed with aqueous sodium chloride solution, dried over magnesium sulfate and evaporated to dryness under reduced pressure. The 13 g of residue was chromatographed over silica gel and eluted with a 6-3-1 cyclohexanechloroform-triethylamine mixture to obtain 8.7 g of 1-methyl-4-(1-methyl-1,2,5,6-tetrahydropyridin-3-yl)-1H-indole.

8.7 g of the said product were dissolved in 87 ml of isopropanol and a solution of 2.4 g of oxalic acid in 48 ml of isopropanol was added thereto. Crystallization was induced and the mixture was iced for 16 hours and vacuum filtered. The recovered product was washed with isopropanol and dried at 50° C. under reduced pressure to obtain 4.3 g of 1-methyl-4-(1-methyl-1,2,5,6-tetrahydropyridin-3-yl)-1H-indole acid oxalate melting at 173° C.

EXAMPLE 25

1-cyclopropylmethyl-3-(1H-indol-4-yl)-3-piperidinol 17.8 g of sodium carbonate and 6.4 g of chloromethylcyclopropane were added to a mixture of 14 g of 3-(1H-indol-4-yl)-3-piperidinol hydrochloride in 250 ml of dimethylformamide and the mixture was stirred under an inert atmosphere at 70° C. for 8 hours. The mixture was stirred at room temperature for 15 hours and was diluted with water. The mixture was extracted with ethyl acetate and the organic phase was washed with water, dried over magnesium sulfate and filtered. The filtrate was evaporated to dryness under reduced pressure at 50° C. to obtain 13.6 g of residue which was chromatographed over silica gel. Elution with a 6-3-1 cyclohexane-chloroformtriethylamine mixture yielded 10 g of 1-cyclopropylmethyl-3-(1H-indol-4-yl)-3-piperidinol with an Rf=0.15.

EXAMPLE 26

4-[1-cyclopropylmethyl-1,2,5,6-tetrahydropyridin-3-yl]-1H-indole phosphate

A solution of 10 g of the product of Example 25 in 300 ml of 1 N hydrochloric acid was refluxed for 6 hours and was then cooled to room temperature and was diluted with 300 ml of water. The mixture was extracted with ethyl acetate and the organic phase was washed with aqueous sodium chloride and evaporated to dryness under reduced pressure. The 9.1 g of residue were chromatographed over silica gel and eluted with a 95-5 chloroform-methanol mixture to obtain 5.4 g of 4-[1-cyclopropylmethyl-1,2,5,6-tetrahydropyridin-3-yl)-1H-indole with an Rf=0.10.

4.9 g of the said product were dissolved in 300 ml of isopropanol and a solution of 10% phosphoric acid in isopropanol was added thereto until the pH was acidic. The mixture was filtered and the recovered product was washed with isopropanol, dried at 50° C. under reduced pressure, crystallized from a mixture of ethanol and methanol and then from water to obtain 4.5 g of 4-[1-cyclopropylmethyl-1,2,5,6-tetrahydropyridin-3-yl]-1H-indole phosphate melting at 230° C.

EXAMPLE 27

1-(2-propenyl)-3-(1H-indol-4-yl)-3-piperidinol 22.9 g of sodium carbonate and 7.6 ml of allyl bromide were added to a mixture of 18 g of 3-(1H-indol-4-yl)-3-piperidinol hydrochloride in 350 ml of dimethylformamide and the mixture was stirred under an inert atmosphere at room temperature for 2 hours. Then, one liter of water and 500 ml of ethyl acetate were added thereto and the decanted organic phase was washed with water, dried and evaporated to dryness under reduced pressure. The 17 g of residue were chromatographed over silica gel and eluted with a 6-3-1 cyclohexanechloroform-triethylamine mixture to obtain 14 g of 1-(2-propenyl)-3-(1H-indol-4-yl)-3-piperidinol with an Rf=0.15.

EXAMPLE 28

4-[1-(2-propenyl)-1,2,5,6-tetrahydropyridin-3-yl]-1H-indole neutral oxalate

A solution of 14 g of the product of Example 27 in 400 ml of hydrochloric acid was refluxed for 4 hours and the mixture was iced and made alkaline with sodium hydroxide. Potassium carbonate was added to the mixture which was then extracted with ethyl acetate. The organic phase was dried and evaporated to dryness under reduced pressure and the 12.7 g of residue were chromatographed over silica gel. Elution with a 9-1 chloroform-acetone mixture yielded 6.85 g of 4-[1-(2-propenyl)-1,2,5,6-tetrahydropyridin-3-yl]-1H-indole with an Rf=0.15.

6.8 g of the said product were dissolved in 400 ml of refluxing isopropanol and 3.6 g of oxalic acid dihydrate were added thereto. The mixture was refluxed for about 15 minutes and then cooled and filtered. The recovered product was dried to obtain 6.4 g of 4-[1-(2-propenyl)-1,2,5,6-tetrahydropyridin-3-yl]-1H-indole neutral oxalate melting at 225° C.

EXAMPLE 29

1-methyl-4-(3-piperidyl)-1H-indole hydrochloride

STEP A: 4-chloro 1-methyl-1H-indole

A mixture of 60 g of 4-chloro-1H-indole, 400 ml of benzene, 200 ml of a 50% solution of sodium hydroxide, 68 g of n-tetrabutylammonium acid sulfate and 68 ml of methyl iodide was heated at 40° C. with agitation for 4 hours and was then cooled and decanted. The aqueous phase was extracted with ethyl acetate and the combined organic phases were washed with a saturated aqueous solution of sodium chloride, dried and distilled to dryness under reduced pressure. The residue was purified by chromatography on silica gel and elution with an 8-2 mixture of cyclohexane and benzene to obtain 63.85 g of 4-chloro-1-methyl 1H-indole.

STEP B: 3-[1-methyl-1H-indole-4-yl]-1-benzyl-3-piperidinol hydrochloride 12 g of magnesium were introduced into 155 ml of tetrahydrofuran and the mixture was refluxed. A solution of 38 g of 1-methyl-4-chloro-1H-indole and 4.5 ml of 1,2-dibromomethane in 115 ml of tetrahydrofuran was slowly introduced after initiation with a few drops of methyl iodide and the reflux was maintained for 6 hours. The mixture was then cooled to 45° C. to obtain a solution of the magnesium derivative which was used as is.

A solution of N-benzyl-3-piperidone prepared from 50 g of N-benzyl-3-piperidone hydrochloride in 115 ml of tetrahydrofuran was introduced dropwise into the solution obtained above and the mixture was heated for 2 hours at reflux, allowed to cool and stirred for 16 hours in an ice bath. 200 ml of saturated ammonium chloride solution were added dropwise and the mixture was filtered. The filter was rinsed with water and with ethyl acetate and the decanted aqueous phase was extracted again with ethyl acetate. The organic phase was washed with a saturated aqueous solution of sodium chloride and was distilled to dryness under reduced pressure. The residue was taken up in ether and the solution was extracted with N hydrochloric acid, made alkaline, re-extracted with ethyl acetate and distilled to dryness under reduced pressure to obtain 73.4 g of crude product. The residue was purified by chromatography over a column of silica and elution with a 9-1 cyclohexane-triethylamine mixture. The product was taken up in methylene chloride and the solution was filtered and distilled to dryness under reduced pressure to obtain 60.5 g of the desired base.

The said base was dissolved in 300 ml of ethyl acetate and a solution of hydrochloric acid in ethyl acetate was added dropwise until the pH was 4. The mixture was chilled for 16 hours and filtered and the recovered product was washed with ethyl acetate and dried at 50° C. under vacuum to obtain 59.6 g of 3-[1-methyl-1H-indole-4-yl]-1-benzyl-3-piperidinol hydrochloride melting at 250° C.

STEP C: 3-(1-methyl-1H-indole-4-yl)-3-piperidinol hydrochloride 50 g of hydrochloride of Step A in 1.5 liters of methanol was hydrogenated at 40° C. in the presence of 15 g of palladized active charcoal. The mixture was then cooled and the catalyst was filtered off. The filtrate was distilled to dryness under vacuum to obtain 37 g of 3-(1-methyl-1H-indole-4-yl)-3-piperidinol hydrochloride with an Rf=0.3 [Support: silica—Eluant: chloroform-methanol-triethylamine (6:3:1)].

STEP D: 1-methyl-4-(3-piperidyl)-1H-indole hydrochloride 5.14 g of hydrochloride of Step B, 80 ml of tetrahydrofuran and 40 ml of anhydrous ethanol were introduced at −40° C. into 400 ml of ammonia and 2.8 g of lithium were then added thereto over one and a half hours in small portions. The ammonia was allowed to evaporate at ambient temperature and then the residue was taken up with 400 ml of water. The solution was extracted with chloroform containing 10% methanol, was washed with water and dried. The mixture was filtered and the filtrate was evaporated to dryness to obtain the free base which was used as is.

The free base was dissolved in ethanol and then a saturated solution of hydrochloric acid in ethanol was added thereto until the pH was 4. The mixture was filtered and the recovered product was washed with ethanol, dried and crystallized from ethanol to obtain 3.0 of 1-methyl-4-(3-piperidyl)-1H-indole hydrochloride melting at 270° C.

Analysis: $C_{14}H_{19}ClN_2$; molecular weight=250.775. Calculated: %C 67.05; %H 7.64; %Cl 14.14; %N 11.17. Found: %C 67.2; %H 7.6; %Cl 14.1; %N 11.1.

EXAMPLE 30

1-methyl-4-(1-propyl-3-piperidyl)-1H-indole oxalate

A mixture of 5 g of the product of Example 29 in 50 ml of dimethylformamide was stirred under an inert atmosphere and 6.3 g of sodium carbonate and 2.05 ml of propyl iodide were added thereto. The mixture was stirred for 16 hours and was then poured into 250 ml of water. The mixture was extracted with ethyl acetate and the organic phase was washed with a saturated aqueous solution of sodium chloride, dried and distilled to dryness under reduced pressure. The residue was purified by chromatography on silica and eluted with a 6-3-1 mixture of cyclohexane-chloroform-triethylamine to obtain 4.9 g of the free base.

4.8 g of the free base were dissolved, with heating, in 15 ml of ethanol and a solution of 2.36 g of oxalic acid in 10 ml of ethanol was added thereto. The mixture was cooled and crystallization was initiated. The mixture was chilled for 16 hours and filtered. The recovered product was washed with ethanol, dried at 50° C. under reduced pressure and crystallized from ethanol to obtain 5.68 g of 1-methyl-4-(1-propyl-3-piperidyl)-1H-indole oxalate with a melting point of ≃167° C.

Analysis: $C_{19}H_{26}N_2O_4$; molecular weight=346.427. Calculated: %C 65.87; %H 7.57; %N 8.09. Found: %C 66.2; %H 7.6; %N 8.1.

EXAMPLE 31

4-(1-ethyl-3-piperidyl)-1H-indole neutral fumarate

STEP A: 4-chloro-1-benzyl-1H-indole

A mixture of 16.9 g of 4-chloro-1H-indole, 170 ml of benzene, 85 ml of a 50% solution of sodium hydroxide, 1.89 g of n-tetrabutylammonium acid sulfate and 16.6 ml of benzyl chloride was heated at 60° C. with strong agitation for 4 hours and was then cooled to ambient temperature and decanted. The organic phase was washed with water, dried and evaporated to dryness to obtain 30.2 g of product. The latter was chromatographed over silica and eluted with cyclohexane to obtain 22.8 g of 4-chloro-1-benzyl-1H-indole melting at 58°-60° C.

STEP B: 1-benzyl-3-[1-benzyl-1H-indole-4-yl]-3-piperidinol hydrochloride 113 g of magnesium were introduced into 200 ml of tetrahydrofuran and the mixture was refluxed. Then, a solution of 184 g of 4-chloro-1-benzyl-1H-indole and 20 ml of 1,2-dibromomethane in 300 ml of tetrahydrofuran was introduced slowly. The reaction mixture was refluxed for 3 hours and was cooled to 30° C. to obtain a solution of the magnesium derivative which was used as.

A solution of 128 g of N-benzyl-3-piperidone in 250 ml of tetrahydrofuran was introduced into the latter solution without exceeding 35° C. and the mixture was refluxed for 2 hours and cooled to 20° C. 1 liter of saturated aqueous ammonium chloride solution was slowly added thereto and the reaction mixture was taken up in 2 liters of ethyl acetate. The mixture was filtered and the filtrate was decanted. The aqueous phase was extracted with ethyl acetate and the organic phase was washed with water, dried and evaporated to dryness to obtain 330 g of a product. The latter was chromatographed over silica and was eluted with a 9-1 mixture of cyclohexanetriethylamine to obtain 218.4 g of a product. The latter was dissolved in ethyl acetate and the solution was extracted with 1 N hydrochloric acid. The aqueous acidic phase was made alkaline with ammonium hydroxide and was extracted with ethyl acetate. The organic phase was dried and 100 ml of saturated solution of hydrochloric acid in ethyl acetate were added thereto. The mixture was filtered and the recovered product was washed with ethyl acetate and with ether and dried to to obtain 194 g of 1-benzyl-3-[1-benzyl-1H-indole-4-yl]-3-piperidinol hydrochloride melting at 185° C. By crystallization from ethyl acetate containing 10% of methanol, the pure product melted at 190° C.

The free base is obtained by treatment with sodium hydroxide and extraction with ethyl acetate and evaporation of the solvent.

STEP C: 3-(1H-indol-4-yl)-1-benzyl-3-piperidino/hydrochloride

A solution of 14.8 g of 1-benzyl-3-[1-benzyl-1H-indol-4-yl]-3-piperidinol in 250 ml of tetrahydrofuran was added at −40° C. to 500 ml of ammonia. Gradually, 1.5 g of sodium were added while the temperature was maintained at −40° C. and at the end of the reaction, ammonium chloride was added until discoloration of the blue tint obtained above. The residue was taken up in water, decanted and was extracted with ethyl acetate, washed with water, dried and evaporated to dryness to obtain 12 g of the free base.

The free base was dissolved in ethyl acetate and a saturated solution of hydrochloric acid in ethyl acetate was added thereto. The mixture was filtered and the recovered product was washed with ethyl acetate and dried to obtain 12.7 g of 3-(1H-indol-4-yl)-1-benzyl-3-piperidinol hydrochloride melting at 228°-230° C.

STEP D: 3-(1H-indol-4-yl)-3-piperidinol hydrochloride 12.7 g of the hydrochloride of Step C in 500 ml of methanol were hydrogenated at 60° C. in the presence of 3.6 g of palladized active charcoal and the mixture was filtered. The filtrate was concentrated to dryness to obtain 9 g of 3-(1H-indol-4-yl)-3-piperidinol hydrochloride which was used as is for the next step.

STEP E: 4-(3-piperidyl)-1H-indole hydrochloride 1.2 g of hydrochloride of Step D, 20 ml of tetrahydrofuran and 10 ml of anhydrous ethanol were added at −40° C. to 100 ml of ammonia and then, over one hour in small portions, 700 mg of lithium were added. The ammonia was allowed to evaporate at ambient temperature and the residue was taken up in 100 ml of water. The mixture was extracted with chloroform containing 10% of methanol and the organic phase was washed with water, dried, filtered and evaporated to dryness. 950 mg of residue were chromatographed over silica and eluted with a 7-2-1 mixture chloroform-methanol-triethylamine to obtain 665 mg of free base.

2.3 g of the free base were dissolved in 50 ml of ethyl acetate and a saturated solution of hydrochloric acid in ethyl acetate was then added thereto. The mixture was filtered and the recovered product was washed with ethyl acetate and dried and the product obtained was crystallized from acetonitrile containing 20% of methanol to obtain 2.2 g of 4-(3-piperidyl)-1H-indole hydrochloride.

STEP F: 4-(1-ethyl-3-piperidyl)-1H-indole neutral fumarate

A mixture of 4.4 g of the hydrochloride of Step E in 90 ml of dimethylformamide was agitated for 5 hours under an inert atmosphere with 5.9 g of sodium carbonate and 1.7 ml of ethyl bromide and was then poured into water. The mixture was extracted with ethyl acetate and the organic phase was washed with water, dried, filtered and evaporated to dryness under reduced pressure at 50° C. The residue was purified by chromatography over silica and elution with a 6-3-1 mixture of cyclohexane-chloroform-triethylamine to obtain 4.3 g of free base.

The free base was dissolved in 200 ml of isopropanol and 2.3 g of fumaric acid were added. The mixture was refluxed for 15 minutes and then was chilled and filtered. The recovered product was dried under reduced pressure and crystallized from methanol to obtain 4.3 g of 4-(1-ethyl-3-piperidyl)-1H-indole neutral fumarate melting at ≃265° C.

Analysis: $C_{17}H_{22}N_2O_2$; molecular weight=286.377. Calculated: %C 71.30; %H 7.74; %N 9.78. Found: %C 71.5; %H 7.8; %N 9.7.

EXAMPLE 32

4-(1-ethyl-1,2,5,6-tetrahydro-3-pyridyl)-1H-indole phosphate

STEP A: 1-ethyl-3-(1H-indole-4-yl)-3-piperidinol

A mixture of 10 g of 3-(1H-indol-4-yl)-3-piperidinol hydrochloride in 200 ml of dimethylformamide was agitated for 4 hours under an inert atmosphere with 13.44 g of sodium carbonate and 4.2 ml of ethyl bromide. The mixture was taken up in water and was extracted with ethyl acetate. The organic phase was washed with water, dried, filtered and evaporated to dryness under reduced pressure at 50° C. The residue was purified by chromatography over silica and eluted with a 6-3-1 mixture of cyclohexane-chloroform-triethylamine to obtain 6.6 g of 1-ethyl-3-(1H-indol-4-yl)-3-piperidinol which was used as is for the following step.

STEP B: 4-(1-ethyl-1,2,5,6-tetrahydro-3-pyridyl)-1H-indole phosphate

A mixture of 6.6 g of the product of Step A in 300 ml of an N aqueous solution of hydrochloric acid was refluxed for 4 hours with agitation and under an inert atmosphere and was cooled. The mixture was made alkaline to a pH of 10 with sodium hydroxide solution and was extracted with ethyl acetate. The organic phase was washed with a saturated aqueous sodium chloride solution, dried, filtered and evaporated to dryness at 50° C. under reduced pressure. The mixture was purified by chromatography over silica and elution with a 9-1 mixture of chloroform-methanol. The product was crystallized from isopropyl ether to obtain 3.95 g of free base with a melting point of ≃124° C.

2.95 g of the free base were dissolved in 300 ml of isopropanol and a 10% solution of phosphoric acid in isopropanol was added thereto until the pH was 4. The mixture was refluxed for 15 minutes, chilled and filtered. The recovered product was dried under reduced pressure and crystallized from a 50:50 ethanol-methanol mixture to obtain 3.1 g of 4-(1-ethyl-1,2,5,6-tetrahydro-3-pyridyl)-1H-indole phosphate melting at 212° C.

Analysis: $C_{15}H_{21}N_2O_4P$; molecular weight=324.317.
Calculated: %C 55.55; %H 6.53; %N 8.64; %P 9.55.
Found: %C 55.4; %H 6.5; %N 8.6; %P 9.3.

EXAMPLE 33

Tablets were prepared containing 10 mg of the neutral fumarate of 4-(1-methyl-piperidin-3-yl)-1H-indole and sufficient excipient of talc, starch and magnesium stearate for a final weight of 150 mg.

Tablets were also prepared containing 10 mg of 1-methyl-4-(3-piperidyl)-1H-indole hydrochloride or 20 mg of 1-methyl-4-(1-propyl-3-piperidyl)-1H-indole oxalate or 20 mg of 4-(1-ethyl-1,2,5,6-tetrahydro-3-pyridyl)-1h-indole phosphate or 5 mg of the neutral succinate of 4-[1-benzyl-1,2,5,6-tetrahydropyridin-3-yl]-1H-indole or 2 mg of the neutral fumarate of 4-[1-propyl-piperidin-3-yl]-1H-indole or 5 mg of the neutral oxalate of 4-[1-(2-propenyl)-1,2,5,6-tetrahydropyridin-3-yl]-1H-indole and sufficient excipient of lactose, starch, talc and magnesium stearate for a final weight of 100 mg.

PHARMACOLOGICAL STUDY

A. Rotation behavior after unilateral injury of nigrostriatal bundle

The unilateral leison was effected with male rats weighing about 220 g of unilateral injection into nigrostriatal dopaminergic bundle of 8 μg of 6-hydroxydopamine in a solution of 2 μg per μl by the method of Ungerstedt [Acta. Physiol. Scand., Vol. 82 (1971), supp. 367, p. 69–93]. In the animals, the direct dopaminergic agonists such as apomorphine administered generally induces a rotating behavior in the contralateral direction of the injured side. The test compounds were administered more than 5 weeks after the lesion and the rats were placed in an automatic rotometer which determine the number of rotations effected by each animal in 2 directions.

In this test, the products of Examples 7, 10 and 30 caused the contralateral rotations at a dose of 2 mg/kg, the products of 6 and 12 at a dose of 5 mg/kg, the product of Example 11 at 10 mg/kg and the products of Examples 17 and 28 at 4 and 5 mg/kg, respectively. The results of the test showed that the tested products possessed interesting dopaminergic stimulating activity.

B. Hypotensive Activity

The hypotensive activity was determined on male rats of the Sprague Dawley S.P.F. strain weighing about 300 g and anesthesized with nembutal (50 mg/kg intraveinously). The test compounds were administered intraveinously through the jugular vein and the arterial carotidinal pressure was measured before and after administration of the test compounds. It was determined that the products of Examples 6 and 10 showed a clear hypotensive activity at a dose of 1 mg/kg.

C. Hypobar anoxia in mice

Male mice weighing between 20 to 22 g were fasted for 5 hours and were divided into groups of 10 mice. To determine the survival time, the mice were placed in a hermetic chamber at a pressure of 90 mm Hg by means of a pump. The test products were orally administered 20 minutes before the test with the controls receiving nothing. The results of Table I correspond to the increase in the survival time of the mice compared to the control mice.

TABLE I

| Product of Example | Dose in mg/kg | % Increase in Survival time |
|---|---|---|
| 6 | 50 | 106 |
|  | 10 | 67 |
|  | 2 | 30 |
|  | 25 | 108 |
| 7 | 5 | 26 |
| 12 | 25 | 44 |

D. Platelet antiaggregation effect

The study of platelet aggregation was effected by the method of Born [J. Physiol., Vol. 168 (1963), p. 178] with the aid of a Mustard aggregometer. Neozoic male rabbits were used with samples of blood taken by cardiac puncture. After slow centrifugation of the blood, the obtained plasma rich in platelets was adjusted to a numerical concentration of 300,000 platelets per mm³. The aggregation agent used was collagen at 40 mcg/ml incubated at 33° C. for 5 minutes. The test products were introduced at variable concentrations into the plasma rich in platelets and the variation in the transmission of a light beam through a tube of the plasma rich in platelets was measured to determine when the aggregates made a quantity of light transmission which is more important and the optical density diminished. The inhibition of aggregation induced by collagen for each product at different doses was determined and the results are reported in Table II.

TABLE II

| Product of Example | Final molar concentration | % of decrease of aggregation |
|---|---|---|
| 13 | $1 \times 10^{-3}$ | 100 |
|  | $1 \times 10^{-4}$ | 42 |
|  | $1 \times 10^{-5}$ | 22 |
| 10 | $1 \times 10^{-3}$ | 100 |
|  | $1 \times 10^{-4}$ | 76 |
|  | $1 \times 10^{-5}$ | 11 |
| 11 | $1 \times 10^{-3}$ | 100 |
|  | $1 \times 10^{-4}$ | 100 |
|  | $1 \times 10^{-5}$ | 24 |

E. Stereotyped behavior in the rat

Dopaminergic agonists such as apomorphine, administered by a general route cause in rats stereotyped behavior. In the test, the compound studied was injected intraperitoneally to batches of 5 rats weighing 160±15 g. The animals were placed immediately after the injection in boxes made of Plexiglas (20×27×17 cm) containing wood shavings and were observed every thirty minutes for three hours. The intensity of the stereotyped movements was numbered from 0 to 6 according to the following evaluation criteria: the animal was asleep (0), awake but motionless (1), turned round in the box (2), sniffed (3), licked (4), touched the shavings with its teeth or gnawed (5), bit the shavings or displayed intense gnawing (6) (Psychopharmacology 68, 15–23 (1980)). The product of Example 29 caused stereotyped behavior at the dose of 50 mg/kg.

F. Potentialization of the stereotypy caused by dexamphetamine

The tests were carried out on groups of 5 male rats weighing 150–180 g and each animal was placed individually in a latticed cage (29×25×17 cm) containing a few fragments of wood shavings. A dose of 3 mg/kg dexamphetamine sulfate was injected intraperitoneally half an hour after the intraperitoneal administration of the test product. The behavior of the animal was noted each half-hour for 5 hours with the evaluation recommended by HALLIWELL and Colleagues (Brit. J. Pharmacol. 1964, Vol. 23, p. 330–350). The animal was asleep (0), it was awake but motionless (1), it turned round in the cage (2), it sniffed the cover thereof (3), it licked the walls thereof (4), it touched the shavings or the bars of the cage with its teeth (5), it bit the shavings or the bars of the cage (6). The products of Examples 29, 31 and 32 potentiated stereotypy at the dose of 3 mg/kg, and the product of Example 30 at the dose of 0.6 mg/kg.

G. Acute toxicity

The $DL_{50}$ lethal dose of the different compounds after intraperitoneal adminstration to mice was determined as the maximum dose which did not cause mortality and the results are in Table III.

TABLE III

| Product of Example | $DL_0$ in mg/kg |
|---|---|
| 6 | ≃60 |
| 7 | ≃80 |
| 10 | ≃80 |
| 11 | ≃60 |
| 12 | ≃80 |
| 13 | ≃60 |
| 17 | ≃40 |
| 28 | ≃200 |
| 29 | ≃80 |
| 30 | ≃60 |
| 31 | ≃60 |
| 32 | ≃60 |

Various modifications of the products and methods of the invention may be made without departing from the spirit or scope thereof and it is to be understood that the invention is intended to be limited only as defined in the appended claims.

We claim:

1. A compound selected from the group consisting of compounds of the formula

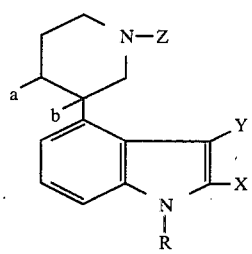

wherein R is selected from the group consisting of hydrogen, alkyl of 1 to 8 carbon atoms and aralkyl of 7 to 12 carbon atoms, X is selected from the group consisting of hydrogen and alkyl of 1 to 8 carbon atoms, Y is selected from the group consisting of hydrogen and halogen, Z is selected from the group consisting of hydrogen, alkyl of 1 to 8 carbon atoms, hydroxyalkyl of 1 to 8 carbon atoms, aryloxyalkyl of 7 to 12 carbon atoms, arylalkyl of 7 to 12 carbon atoms optionally substituted with at least one member of the group consisting of halogen, alkoxy of 1 to 4 carbon atoms, alkyl of 1 to 4 carbon atoms, —OH, —CF$_3$, OCF$_3$, NO$_2$ and NH$_2$, cycloalkylalkyl of 4 to 12 carbon atoms, alkenyl of 3 to 8 carbon atoms and alkynyl of 3 to 8 carbon atoms, a and b may each be hydrogen or form a double bond or a is hydrogen and b is selected from the group consisting of —OH and alkoxy of 1 to 8 carbon atoms and their non-toxic, pharmaceutically acceptable acid addition salts.

2. A compound of claim 1 wherein Y is hydrogen.

3. A compound of claim 1 wherein X is hydrogen.

4. A compound of claim 1 wherein X and Y are hydrogen.

5. A compound of claim 1 wherein Z is hydrogen.

6. A compound of claim 1 wherein Z is selected from the group consisting of alkyl of 1 to 4 carbon atoms and aralkyl of 7 to 12 carbon atoms.

7. A compound of claim 1 wherein a and b form a double bond.

8. A compound of claim 1 wherein a and b are hydrogen.

9. A compound of claim 1 wherein a is hydrogen and b is selected from the group consisting of —OH and methoxy.

10. A compound of claim 1 selected from the group consisting of 4-(1-propyl-1,2,5,6-tetrahydropyridin-3-yl)-1H-indole, 4-(1-methyl-1,2,5,6-tetrahydropyridin-3-yl)-1H-indole, 4-(1-methyl-piperidin-3-yl)-1H-indole, 4-(piperidin-3-yl)-1H-indole, 4-(1,2,5,6-tetrahydropyridin-3-yl)-1H-indole, 4-(1-propyl-piperidin-3-yl)-1H-indole, 1-methyl-4-(3-piperidyl)-1H-indole, 1-methyl-4-(1-propyl-3-piperidyl)-1H-indole, 4-(1-ethyl-3-piperidyl)-1H-indole and 4-(1-ethyl-1,2,5,6-tetrahydro-3-pyridyl)-1H-indole and their non-toxic, pharmaceutically acceptable acid addition salts.

11. A dopaminergic stimulating composition comprising a dopaminergically stimulating amount of at least one compound of claim 1 and an inert pharmaceutical carrier.

12. A composition of claim 11 wherein the active compound is selected from the group consisting of 4-(1-propyl-1,2,5,6-tetrahydropyridin-3-yl)-1H-indole, 4-(1-methyl-1,2,5,6-tetrahydropyridin-3-yl)-1H-indole, 4-(1-methyl-piperidin-3-yl)-1H-indole, 4-(piperidin-3-yl)-1H-indole, 4-(1,2,5,6-tetrahydropyridin-3-yl)-1H-indole, 4-(1-propyl-piperidin-3-yl)-1H-indole, 1-methyl-4-(3-piperidyl)-1H-indole, 1-methyl-4-(1-propyl-3-piperidyl)-1H-indole, 4-(1-ethyl-3-piperidyl)-1H-indole and 4-(1-ethyl-1,2,5,6-tetrahydro-3-pyridyl)-1H-indole and their non-toxic, pharmaceutically acceptable acid addition salts.

13. A composition of claim 11 wherein the active compound is selected from the group consisting of 4-(piperidin-3-yl)-1H-indole hydrochloride and the neutral fumarate of 4-(1-propyl-piperidin-3-yl)-1H-indole.

14. A method of inducing dopamingeric stimulating activity in a warm-blooded animal comprising administering to a warm-blooded animal a dopaminergically stimulating amount of at least one compound of claim 1.

15. The method of claim 14 wherein the compound is selected from the group consisting of 4-(1-propyl-1,2,5,6-tetrahydropyridin-3-yl)-1H-indole, 4-(1-methyl-1,2,5,6-tetrahydropyridin-3-yl)-1H-indole, 4-(1-methyl-piperidin-3-yl)-1H-indole, 4-(piperidin-3-yl)-1H-indole, 4-(1,2,5,6-tetrahydropyridin-3-yl)-1H-indole, 4-(1-propyl-piperidin-3-yl)-1H-indole, 1-methyl-4-(3-piperidyl)-1H-indole, 1-methyl-4-(1-propyl-3-piperidyl)-1H-indole, 4-(1-ethyl-3-piperidyl)-1H-indole and 4-(1-ethyl-1,2,5,6-tetrahydro-3-pyridyl)-1H-indole and their non-toxic, pharmaceutically acceptable acid addition salts.

16. The method of claim 14 wherein the compound is selected from the group consisting of 4-(piperidin-3-yl)-1H-indole hydrochloride and the neutral fumarate of 4-(1-propyl-piperidin-3-yl)-1H-indole.

* * * * *

UNITED STATES PATENT AND TRADEMARK OFFICE
CERTIFICATE OF CORRECTION

PATENT NO. : 4,332,808
DATED : June 1, 1982
INVENTOR(S) : JACQUES GUILLAUME et al It is certified that error appears in the above-identified patent and that said Letters Patent is hereby corrected as shown below:

| | | |
|---|---|---|
| Column 5 | Line 40 | "etherification group" should be --etherification agent-- |
| Column 19 | Line 45 | "piperidino/hydrochloride" should be --piperidinol hydrochloride-- |
| Column 22 | Line 24 | "after the row across -7-526 a dividing line |
| Column 22 | Line 52 | After row across 1 x $10^{-5}$-22 a dividing line should follow |
| Column 22 | Line 54 | After row 1 x $10^{-5}$-11 a dividing line should be inserted |

Signed and Sealed this

Fourteenth Day of December 1982

[SEAL]

Attest:

GERALD J. MOSSINGHOFF

Attesting Officer

Commissioner of Patents and Trademarks